(12) United States Patent
Pacetti

(10) Patent No.: US 6,685,737 B1
(45) Date of Patent: Feb. 3, 2004

(54) ENDOLUMINAL STENT CROSS SECTION FOR OPTIMUM BIOCOMPATIBILITY

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 289 days.

(21) Appl. No.: 09/703,664

(22) Filed: Oct. 31, 2000

(51) Int. Cl.[7] .................................................. A61F 2/06
(52) U.S. Cl. ..................................................... 623/1.15
(58) Field of Search ............................. 623/1.15, 1.21, 623/1.1, 1.3, 1.32

(56) References Cited

U.S. PATENT DOCUMENTS

| | | | |
|---|---|---|---|
| 4,760,849 A | 8/1988 | Kropf | |
| 4,787,884 A | 11/1988 | Goldberg | |
| 4,790,809 A | 12/1988 | Kuntz | |
| 4,790,810 A | 12/1988 | Pugh, Jr. et al. | |
| 5,108,417 A | * 4/1992 | Sawyer | 606/191 |
| 5,344,425 A | 9/1994 | Sawyer | |
| 5,476,506 A | 12/1995 | Lunn | |
| 5,496,365 A | 3/1996 | Sgro | |
| 5,613,981 A | 3/1997 | Boyle et al. | |
| 5,718,713 A | * 2/1998 | Frantzen | 623/1.15 |
| 5,824,038 A | 10/1998 | Wall | |
| 5,843,117 A | * 12/1998 | Alt et al. | 606/194 |
| 5,938,695 A | 8/1999 | Borghi | |
| 5,961,546 A | 10/1999 | Robinson et al. | |
| 5,968,092 A | 10/1999 | Buscemi et al. | |

OTHER PUBLICATIONS

Robert S. Schwartz, et al.; Restenosis and the Proportional Neointimal Response to Coronary Artery Injury: Results in a Porine Model; JACC vol. 19, No. 2; Feb. 1992: 267–74; Rochester, Minnesota.

Robert S. Schwartz, et al; Artery Size, Neointima, and Remodeling Time for Some Standards; JACC vol. 32, No. 7; Dec. 1998: 2087–94; Rochester, Minnesota; Cleveland, Ohio; Rotterdan, The Netherlands; Elsevier Science Inc.

Ran Kornowski, et al.; In–Stent Restenosis: Contributions of Inflammatory Responses and Arterial Injury to Neointimal Hyperplasia; JACC vol. 31, No. 1; Jan. 1998: 224–30; Washington, D.C. and San Antonio, Texas; Elsevier Science, Inc.

* cited by examiner

Primary Examiner—John J. Calvert
Assistant Examiner—James G Smith
(74) Attorney, Agent, or Firm—Fulwider Patton Lee & Utecht, LLP

(57) ABSTRACT

A stent design minimizing the disturbance of blood flow and minimizing the trauma caused by the stent to the vessel in which it is implanted. The geometry of the stent struts reduces the neointima hyperplasia caused by trauma to the vessel wall and caused by disturbance to the endothelium created by changes in fluid shear stress. A stent is disclosed that includes struts having an outer surface configured to reduce the injury and inflammation to the vessel wall. The shape of the outer surface of the stent strut that distributes the stress imposed on the vessel wall surface evenly over the stent outer surface is a singular arc whose radii of curvature is such that the vessel wall meets this circular arc at its edge, and at this edge the strut surface slope matches that of the vessel wall. The stent is further configured with struts that have an inner surface with a geometry that reduces the turbulence of the blood flow as it passes over the struts. The inner surface provides a smooth transition at the interface between the strut leading edge and the vessel wall, and provides a smooth transition at the interface between the strut trailing edge and the vessel wall, yielding a wing-like shape to the inner surface of the strut. The overall optimal geometry of the stent strut combines an outer surface that minimizes vessel injury with an inner surface having hydrodynamics that minimizes the disturbance to the blood flow in the vessel.

23 Claims, 5 Drawing Sheets

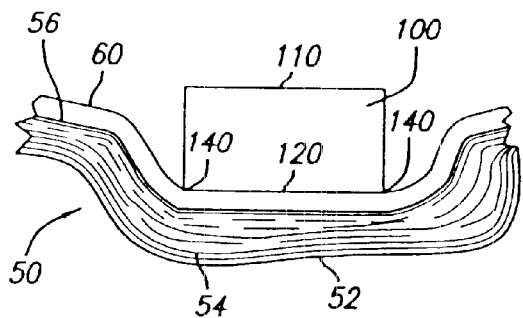
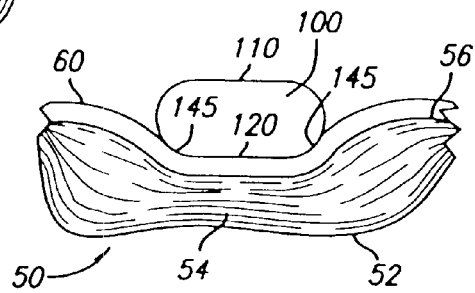
FIG. 3A
FIG. 3B
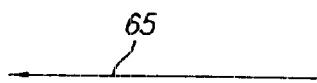
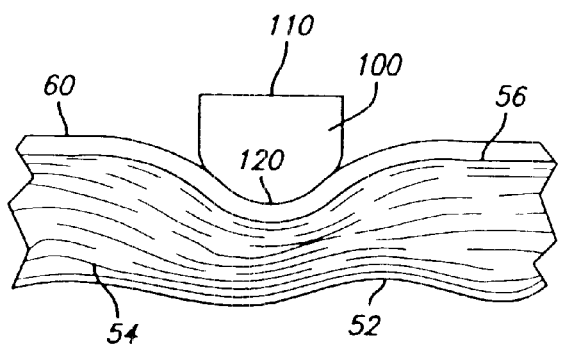
FIG. 4
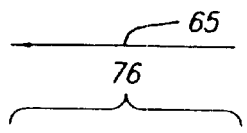
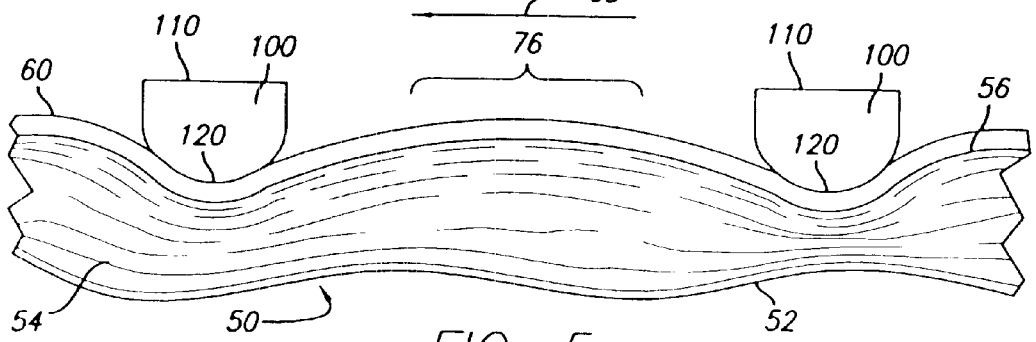
FIG. 5

FIG. 10
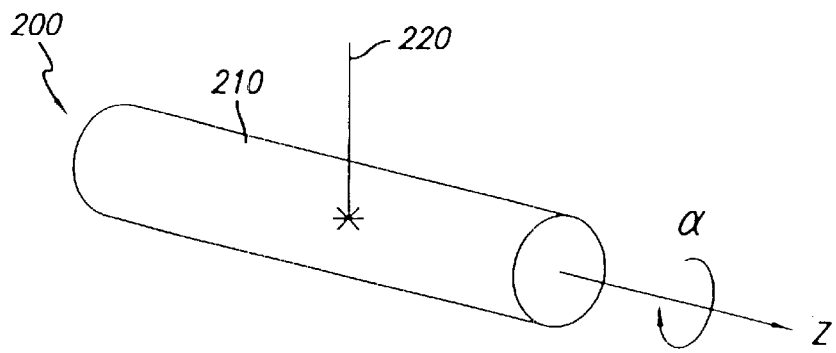
FIG. 11
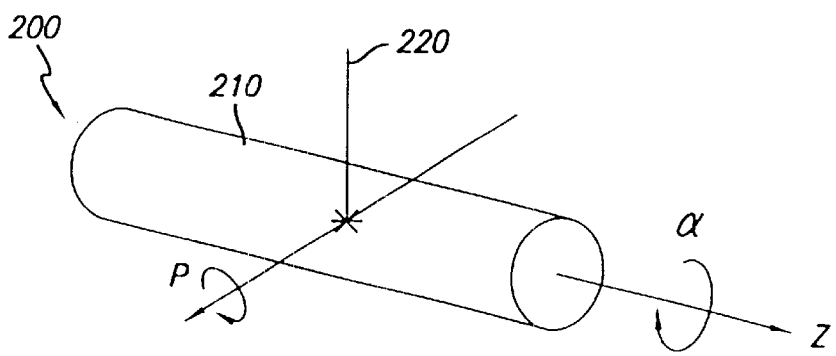
FIG. 12
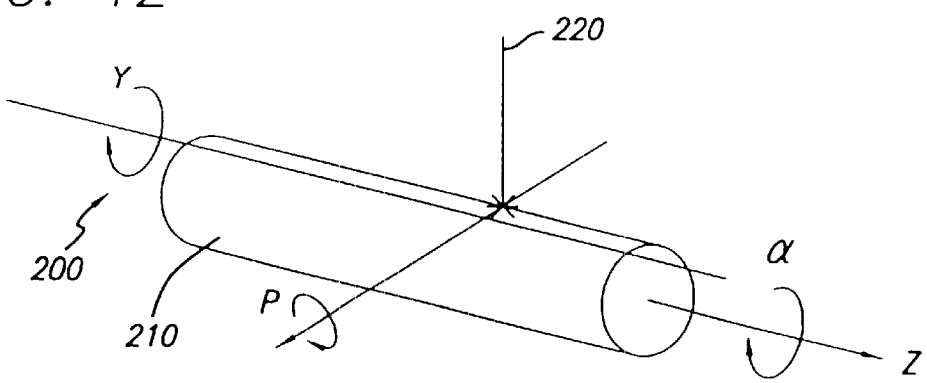
FIG. 13

ENDOLUMINAL STENT CROSS SECTION FOR OPTIMUM BIOCOMPATIBILITY

BACKGROUND OF THE INVENTION

The present invention relates to expandable endoprosthesis devices, generally called stents, which are adapted to be implanted into a patient's body lumen, such as carotid arteries, coronary arteries, peripheral arteries, veins, or other vessels to maintain the patency of the lumen. More particularly, the invention relates to the design and configuration of the geometry of stent struts so as to minimize the disturbance to the blood flow in the vessel, and to minimize the trauma caused by the stent to the body lumen in which it is implanted.

Stents are frequently used in the treatment of atherosclerotic stenosis in blood vessels especially in conjunction with percutaneous transluminal angioplasty (PTA) or percutaneous transluminal coronary angioplasty (PTCA) procedures, with the intent to reduce the likelihood of restenosis of a vessel. Stents are also used to support a body lumen, tack-up a flap or dissection in a vessel, or in general where the lumen is weak to add support. Stents are generally cylindrically shaped devices which function to hold open and sometimes expand a segment of a blood vessel or other arterial lumen, such as a coronary artery. Stents are usually delivered in a compressed condition to the target site and then deployed at that location into an expanded condition to support the vessel and help maintain it in an open position. They are particularly suitable for use in supporting and holding back a dissected arterial lining which can occlude the fluid passageway there through.

Stents or expandable grafts are implanted in a variety of body lumens in an effort to maintain their patency and are especially well-suited for the treatment of atherosclerotic stenosis in blood vessels. Intracoronary stents have become a standard adjunct to percutaneous coronary angioplasty in the treatment of arterial atherosclerotic disease. Although commercial stents vary in design and materials, they share similar structural features. Most stents in clinical use are metallic and are either self-expanding or are expanded by the force of an expandable member, such as an angioplasty dilatation balloon. These devices are typically implanted via a delivery catheter which is inserted at an easily accessible location on the patient and then advanced through the patient's vasculature to the deployment site. The stent is initially maintained in a radially compressed or collapsed state to enable it to be maneuvered through the lumen and into the stenosis. Once in position, the stent is deployed which, depending upon its construction, is achieved either automatically by the removal of a restraint, or actively by the inflation of a balloon about which the stent is carried on the delivery catheter.

The stent must be able to simultaneously satisfy a number of mechanical requirements. First and foremost, the stent must be capable of withstanding the structural loads that are imposed thereon as it supports the lumen walls. In addition to having adequate radial strength or more accurately, hoop strength, the stent should nonetheless be longitudinally flexible to allow it to be maneuvered through a tortuous vascular path and to enable it to conform to a deployment site that may not be linear or may be subject to flexure. The material of which the stent is constructed must allow the stent to undergo expansion, which typically requires substantial deformation of localized portions of the stent's structure. Once expanded, the stent must maintain its size and shape throughout its service life despite the various forces that may come to bear upon it, including the cyclic loading induced by the pulsatile character of arterial blood flow. Finally, the stent must be biocompatible so as not to trigger any adverse vascular responses. A variety of devices are known in the art for use as stents and have included coiled wires in a variety of patterns that are expanded after being placed intraluminally on a balloon catheter, helically wound coiled springs manufactured from an expandable heat sensitive metal, and self-expanding stents inserted into a compressed state for deployment into a body lumen.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

Details of prior art expandable stents can be found in U.S. Pat. No. 3,868,956 (Alfidi et al.); U.S. Pat. No. 4,512,1338 (Balko et al.); U.S. Pat. No. 4,553,545 (Maass, et al.); U.S. Pat. No. 4,733,665 (Palmaz); U.S. Pat. No. 4,762,128 (Rosenbluth); U.S. Pat. No. 4,800,882 (Gianturco); U.S. Pat. No. 5,514,154 (Lau, et al.); U.S. Pat. No. 5,421,955 (Lau et al.); U.S. Pat. No. 5,603,721 (Lau et al.); U.S. Pat. No. 4,655,772 (Wallsten); U.S. Pat. No. 4,739,762 (Palmaz); and U.S. Pat. No. 5,569,295 (Lam). Further details of prior art self-expanding stents can be found in U.S. Pat. No. 4,580,568 (Gianturco); and U.S. Pat. No. 4,830,003 (Wolff, et al.).

Despite the widespread use of intracoronary stents, in-stent restenosis remains a major clinical problem; however, restenosis does not develop in all patients undergoing coronary angioplasty and stent implantation. The mechanism of restenosis after stent implantation is principally neointimal hyperplasia, as stents resist negative arterial remodeling. Relative to PTCA alone, stents improve the outcome by minimizing vessel recoil, reducing plaque prolapse, and affecting long term remodeling.

It has been shown that smooth muscle cell (SMC) proliferation is affected by signaling from the endothelium. In flowing blood, the endothelium seeks a surface shear stress of approximately fifteen dynes/cm$^2$. This tendency is known as the "Glagov Effect." If the shear stress is too high, the endothelial cells signal the smooth muscle cells to relax. When the detected shear stress is low, the endothelium signals for the vessel to constrict. If the shear stress remains consistently low, SMC proliferation occurs causing lumenal narrowing. Regions of flow reversal, or disturbed blood flow, also cause the endothelial cells to signal for lumenal narrowing in an effort to maintain the desired shear stress. This is one reason why atherosclerotic legions form first at vessel bifurcations and other regions of complex flow. Another reason is that in these regions there is an increased residence time of blood elements including atherogens such as lipids and cholesterol which increases the chance of deposition. It is known that stent struts alter the blood flow. Immediately upstream and downstream of the struts, the flow is disturbed, with flow reversals and eddies. Thus, the introduction of the stent into the vessel can cause lumenal narrowing and potentially sets the stage for further atherosclerotic disease.

Animal studies also have established a significant correlation between the degree of arterial injury caused by metallic stents and the resultant neointimal thickness and lumen stenosis at the stented site. Patients with restenosis may be those whose vessel incurred greater injury during revascularization. Indeed, breakage of the internal elastic lamina (IEL) has been correlated with a higher level of restenosis. Similarly, higher injury score has been implicated as a causal factor in neointimal formation, resulting in restenosis. In addition, inflammation caused by the implantation of the stent may cause neointimal growth, and a deeper arterial laceration causes a greater inflammatory reaction. Thus, the amount of neointimal formation may be proportional to the degree of vessel injury, the extent of inflammatory reaction, or both, independently or in combination, wherein the deep arterial lacerations cause the thickest neointima leading to a more severely compromised lumen. Stent design, its geometric configuration, and the amount of surface metal coverage also affects the degree of vessel wall injury, the resulting inflammatory response, and the quality of neointima formed after implantation of the stent.

What has been needed, and heretofore unavailable, in the art of stent design is a geometric configuration of the stent struts which minimizes neointimal growth. Such a design should reduce the disturbance of the blood flow within the vessel. Moreover the optimal stent geometry should reduce the injury and inflammation of the vessel wall. The present invention satisfies these and other needs.

SUMMARY OF THE INVENTION

Briefly, and in general terms, the present invention is directed to the design and configuration of stents that will minimize the disturbance of blood flow in the vessel and that will minimize the trauma caused by the stent to the vessel wall in which it is implanted. The stent of the present invention includes struts having an outer surface configured with a geometry that contacts a vessel wall so as to reduce the injury, and inflammation, to the several layers of the vessel wall. In addition, the stent struts have an inner surface that contacts the blood flow, wherein the inner surface is configured with a geometry that reduces the turbulence of the blood flow as it passes over the struts. Moreover, the shape of the outer surface may be different from the shape of the inner surface. Such a configuration reduces the disturbance to the endothelium created by changes in fluid shear stress, and minimizes trauma to the vessel wall, leading to a decrease in neointimal hyperplasia.

Despite the widespread use of intracoronary stents, in-stent restenosis remains a major clinical problem. Restenosis after stent implantation is principally caused by neointimal hyperplasia. It has been shown that smooth muscle cell proliferation is affected by signaling from the endothelium for lumenal narrowing. Immediately upstream and downstream of the struts, the flow is disturbed, with flow reversals and eddies. In addition, breakage of the internal elastic lamina and inflammation caused by the implantation of the stent has been correlated with a higher level of restenosis. Stent design, specifically the geometric configuration of the stent struts, can affect the amount of vessel wall injury and inflammation, as well as the shear stress and turbulence of the blood flow over the stent. Thus, the strut geometry may effect neointimal formation after implantation of the stent.

The stent of the present invention has a novel geometric configuration of the outer surface and the inner surface of the stent struts. One particular shape of the outer surface of the stent strut is one that distributes the stress evenly over the stent outer surface. In order to provide good vessel scaffolding, while only covering the minimal amount of vessel wall area, stent struts have a high aspect ratio being longer than they are wide. Starting with the stent structure, the present invention describes outer and inner strut surfaces. The geometry of these surfaces can be largely defined by a cross-section, as struts are typically constant in cross-section along their length. This invention discloses particular stent cross-sections, which minimize the stress applied to the vessel wall and the disturbance to the blood flow. Many orientations relative to the strut itself are possible for this strut cross-section. The stent cross-section referred to herein lies in the plane that intersects the central axis of the vessel. In this discussion, the vessel is cylindrical and straight. This plane is coincident with the direction of blood flow and lies perpendicular to the hoop stress that a stent exerts on the vessel. Within a deployed stent, the struts may lie in a variety of orientations relative to the vessel axis. In all cases, this optimum strut cross-sectional geometry is defined along this plane that is, of course, parallel to and intersects the vessel axis. The shape of the outer surface of the stent that distributes the stress imposed on the inner elastic lamina evenly over the stent outer surface is a singular circular arc. In one aspect of the present invention, the arc is one whose radii of curvature is such that at the strut edge, the stent surface slope matches that of the vessel wall. The radius of curvature (r) of the strut outer surface can be calculated as a function of the strut width (W) and the angle ($\theta$) with which the vessel wall intercepts the stent strut. The radius of curvature can then be defined as: $r = W \div (2 \sin \theta)$. In this configuration, the outer surface is symmetric relative to a radial vector, this vector being defined as running from the vessel axis outwards towards the vessel wall.

An optimal geometry of the stent inner surface is one in which the shape disturbs the blood flow the least. To minimize the disturbance of blood flow, the inner surface should provide a smooth transition at the interface between the strut leading edge and the vessel wall. Likewise, there should be a smooth transition at the interface between the strut trailing edge and the vessel wall. However, the shape of the ideal inner surface is also a function of the strut width and the amount of strut cross-sectional area needed for strength, and may not be symmetric with respect to a radial vector. Providing strength to the stent, while providing hydrodynamics that minimizes the disturbance to the blood flow, yields a wing-like (foil) shape to the inner surface of the strut. Thus, the overall optimal geometry of the stent strut of the present invention combines an outer surface that minimizes vessel injury with an inner surface whose hydrodynamics minimizes the disturbance to the blood flow in the vessel.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 3A depicts a cross-sectional view of a rectangular shaped stent strut implanted within a vessel wall.

FIG. 3B depicts a cross-sectional view of an oval shaped stent strut implanted within a vessel wall.

FIG. 4 depicts a cross-sectional view of an embodiment of a stent strut of the present invention having an outer surface configured to minimize trauma to the vessel wall.

FIG. 5 depicts a cross-sectional view of a vessel wall having two stent struts of the present invention implanted therein, showing the parabolic nature of the vessel wall between the struts.

FIG. 10 depicts a perspective view of a metal tube being rotated about the longitudinal (Z) axis for laser cutting.

FIG. 11 depicts a perspective view of a metal tube being rotated about the longitudinal (Z) axis and its pitch (P) for laser cutting.

FIG. 12 depicts a perspective view of a metal tube being rotated about the longitudinal (Z) axis, its pitch (P) and its yaw (Y) for laser cutting.

FIG. 13 depicts a cross-sectional view of a rough cut stent strut being electropolished into a foil shape.

DESCRIPTION OF THE PREFERRED EMBODIMENTS

Figure 1A:
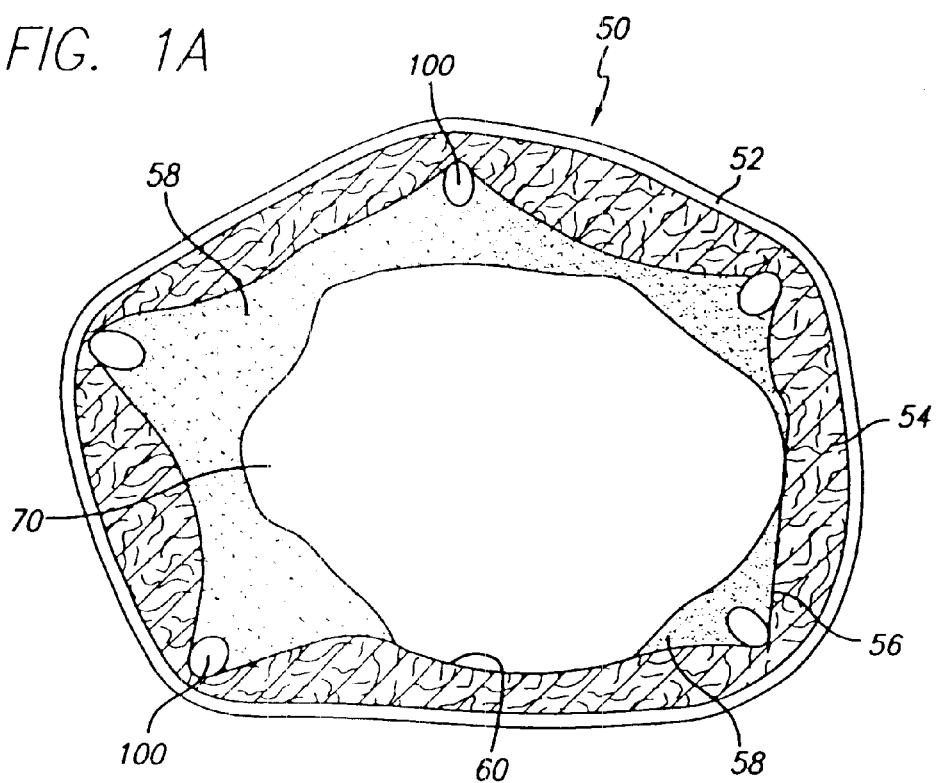
FIG. 1 depicts a cross-sectional view of a vessel wall having a stent implanted therein, including neointima growth.

As shown in the drawings for purposes of illustration, the present invention is directed to the design and configuration of stents so as to minimize the disturbance of blood flow and to minimize the trauma caused by the stent to the vessel wall in which it is implanted. The stent of the present invention includes struts having an outer surface configured with a geometry so as to reduce the injury and inflammation to the several layers of the vessel wall in which it is imbedded. In addition, the stent struts have an inner surface that contacts the blood flow, wherein the inner surface is configured with a geometry which reduces the turbulence of the blood flow as it passes over the struts. The stent having strut configurations of the present invention may be used in an identical manner compared to currently available stents. The fact that the stent struts have a certain cross-sectional shape will, in all likelihood, be transparent to the interventionalist.

A focus of recent development work in the treatment of heart disease has been directed to endoprosthetic devices called stents. Despite the widespread use of intracoronary stents, in-stent restenosis remains a major clinical problem. Smooth muscle cell proliferation is affected by signaling from the endothelium. Regions of flow reversal, or disturbed blood flow may cause the endothelial cells to signal for lumenal narrowing. It is known that stent struts alter the blood flow; therefore, the introduction of the stent into the vessel can cause lumenal narrowing. A significant correlation between the degree of arterial injury and inflammation caused by the implantation of metallic stents and the resultant neointimal thickness and lumen stenosis at the stented site has also been established. Thus, breakage of the internal elastic lamina and higher injury score has been implicated as a causal factor in neointimal formation, resulting in restenosis. Stent design, its geometric configuration and the amount of surface metal coverage might also affect the amount of vessel wall injury, the resulting inflammation, and hence neointimal formation after implantation of the stent. The present invention addresses the optimal geometric stent design that will minimize restenosis caused by blood flow disturbance and vessel wall injury.

Figure 1B:
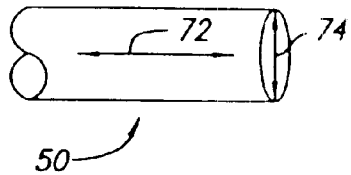

Turning now to the drawings in which reference numerals represent like or corresponding elements in the drawings, and more particularly to FIGS. 1A and 1B, there is shown a cross section of a vessel wall 50, for example a coronary artery, having a stent 100 implanted into the vessel wall. The vessel wall has an external elastic lamina (EEL) 52 surrounding a layer of media 54, which is bounded on the inside of a healthy vessel by an internal elastic lamina (IEL) 56. The innermost layer of the vessel is the endothelium 60, which is the layer of cells that contacts the blood flowing though the vessel lumen 70. In a vessel where a stent has been implanted or other injury to the vessel wall has occurred, a neointima layer 58 is likely to form, especially over the stent struts. With stent implantation, the endothelium is almost completely denuded. A neointimal layer of smooth muscle cells in extracellular matrix proliferates on the lumenal side of the IEL. Typically, complete reendothelialization occurs after much of the neointima has formed. FIG. 1A demonstrates neointima proliferation (hyperplasia) in a stented vessel. The IEL is intact but the compressed media is a type of injury. The vessel wall may also have an outside layer, known as the adventicia (not shown), and may be imbedded or contained within other tissue layers, for example, muscle or skin. For purposes of definition, the vessel has a longitudinal axis 72, which extends lengthwise through the center of the vessel. In addition, the vessel has a radial axis 74, which lies in the radial direction and perpendicular to the longitudinal axis (FIG. 1B).

Figure 2A:
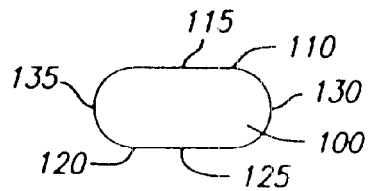
FIG. 2A depicts a cross-sectional view of a stent strut having an oval shape.
Figure 2B:
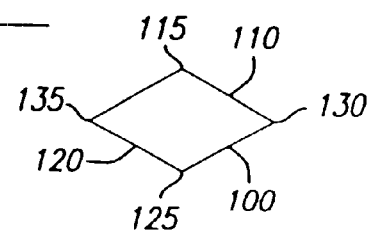
FIG. 2B depicts a cross-sectional view of a stent strut having an diamond shape.
Figure 2C:
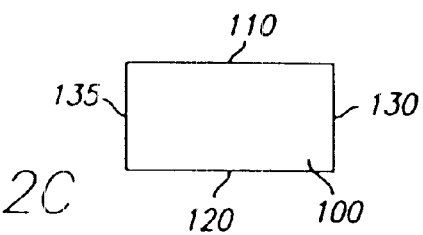
FIG. 2C depicts a cross-sectional view of a stent stent having a rectangular shape.

As shown in FIGS. 2A–2C, the cross section of a stent strut 100 has an inner surface 110 and an innermost point 115, the location depending on the geometry of the inner surface of the stent strut. The inner surface of the strut contacts the blood flow 65. Conversely, the stent has an outer surface 120 that contacts the vessel wall and that is on the opposite side of the stent from the inner surface. The outer surface has an outermost point, which depends on the geometry of the outer surface. The stent geometry also provides for a leading edge or point 130, which is the furthest portion of the strut into the blood flow, and faces the blood flow. Finally, the strut has a trailing edge or point 135, which is the last portion of the stent which the blood contacts while passing over the strut, and faces away from the blood flow. The leading point and trailing point are defined as the point (or edges) where the surface normal is parallel to the vessel longitudinal axis. Additionally, the surface tangent at these points is parallel to the vessel radial axis. These points separate the inner surface and outer surface of the stent strut.

Typical prior art stent geometries include cross sections which are round or oval (FIG. 2A), rhombus or diamond shaped (FIG. 2B), and square or rectangular (FIG. 2B). None of these shapes are optimal for minimizing injury to the blood vessel wall, nor are they optimal for minimizing the disturbance of blood flow within the vessel. In configurations of a square or rectangle with rounded corners, the leading and trailing points are defined as the as the midpoints of the leading and trailing edges, respectfully. In a similar manner, the innermost and outermost points are defined as the as the midpoints of the inner and outer surfaces, respectfully.

If the geometry of the stent strut 100 is the same for the inner surface 110 and the outer surface 120, then the strut is symmetric with respect to the vessel longitudinal axis 72. If the inner surface of the strut is symmetric with respect to its innermost point 115, then the inner surface is symmetric with respect to the vessel radial axis 74. The same holds true for the outer surface, where if the outer surface is symmetric with respect to the outermost point 125, then the outer surface is also symmetric with respect to the vessel radial axis.

As the outer surface 120 of a stent strut 100 lies against the wall of the vessel 50, it has a role in the acute reaction of the vessel wall to the stent. A smooth outer surface is beneficial to reducing the injury to and inflammation of the vessel wall, since the endothelium 60 is damaged less as the stent is deployed and the struts "scissor" apart. A very rough stent strut surface might be expected to cause more vessel injury. The strut cross-sectional shape also is a factor that affects vessel injury and dissection. The best stent outer shape that reduces injury to the vessel wall is one that distributes the stress concentrated in the IEL 56 evenly over the outer stent surface. The stress created on the vessel wall by the outer surface of a stent having a cross-section in the shape of a rectangle with sharp edges 140 (FIG. 3A) or rounded edges 145 (FIG. 3B) is higher at the edges. Vessel injury, potential rupture of the IEL, and inflammation are likely to occur at these high stress points.

Referring to FIG. 4, which depicts the cross-section of a deployed stent of the present invention 100 where the section is taken longitudinally along the center of the vessel 50, the outer shape of the stent strut is one that distributes the stress evenly over the stent outer surface 120. Thus, the shape of the outer surface may be different from the shape of the inner surface 110. As shown in FIG. 5, the vessel wall assumes a shape 74 between the struts that is approximately parabolic. If the geometry were purely two dimensional, then the shape of the vessel wall would be a catenary. However, in the case of a three dimensional vessel, it is likely a more complex shape. For purposes of this discussion, the stent is assumed to be deployed in an ideal manner. The shape of the outer surface 120 of the stent that distributes the stress imposed on the IEL 56 evenly over the stent outer surface is a singular circular arc. The arc should be one whose radius of curvature is such that, at the edges, the stent surface slope matches that of the vessel wall. Specifically, where the stent surface touches the surface of the vessel wall and the arc formed by the stent outer surface is a circular arc, then the two surfaces, where they first meet, are tangent. Such a configuration of the outer surface will likely be symmetric relative to a radial vector. For a given stent outer surface area and width, this circular arc is the stent outer shape that could be deployed to the highest stress without perforating the intima or IEL.

Figure 6:
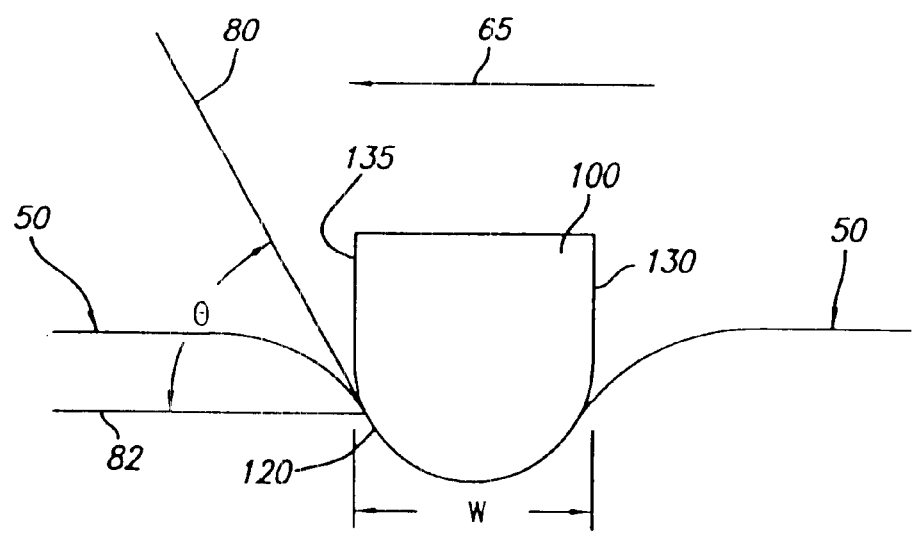
FIG. 6 depicts a schematic representation of an embodiment of a stent strut of the present invention, showing the radius of curvature of the outer surface of the strut.

Referring to FIG. 6, The radius of curvature (r) of the stent outer surface 120 can be calculated as a function of the stent width (W) and the angle (θ) with which the vessel wall 50 intercepts the stent strut 100. The stent width (W) is measured as the distance between the leading edge 130 and the trailing edge 135. The intercept angle (θ) is defined as the angle between the horizontal plane 82 and the slope of the line (tangent) 80 where the vessel wall meets the stent strut. This angle is present when the stent is deployed in an ideal manner with regards to good stent apposition to the vessel wall but with minimal injury. The preferred radius of curvature (r) is then defined as: r=W÷(2sin θ).

Figure 7:
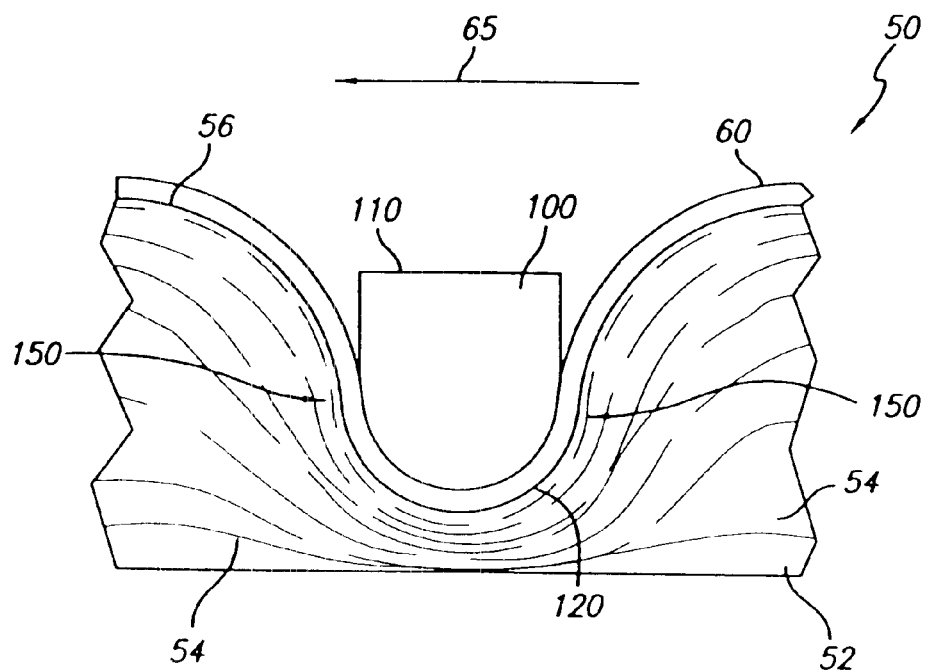
FIG. 7 depicts a cross-sectional view of an embodiment of a stent strut of the present invention having an outer surface configured to minimize trauma to the vessel wall, wherein the stent is incorrectly deployed in the vessel wall.

However, even if the stent outer surface is configured with this radius of curvature, the stress in the IEL 56 will not be evenly distributed if the stent is improperly deployed. As shown in FIG. 7, if the stent is deployed too deeply into the vessel wall 50, then areas of high stress 150 will be created. Consequently, to minimize vessel injury and neointimal growth, the stent should be deployed such that the vessel wall meets the circular arc at its edge. At this point, the slope of the vessel wall and the slope at the edge of the stent strut will, necessarily, be tangent. Furthermore, it may be advantageous to augment the shape of the outer surface 120 at transition zones where the outer surface meets the leading edge 130 and the trailing edge 135 of the stent strut 100. At such transition zones, the outer surface would not necessarily have the same radius of curvature as the rest of the outer surface.

Figure 8:
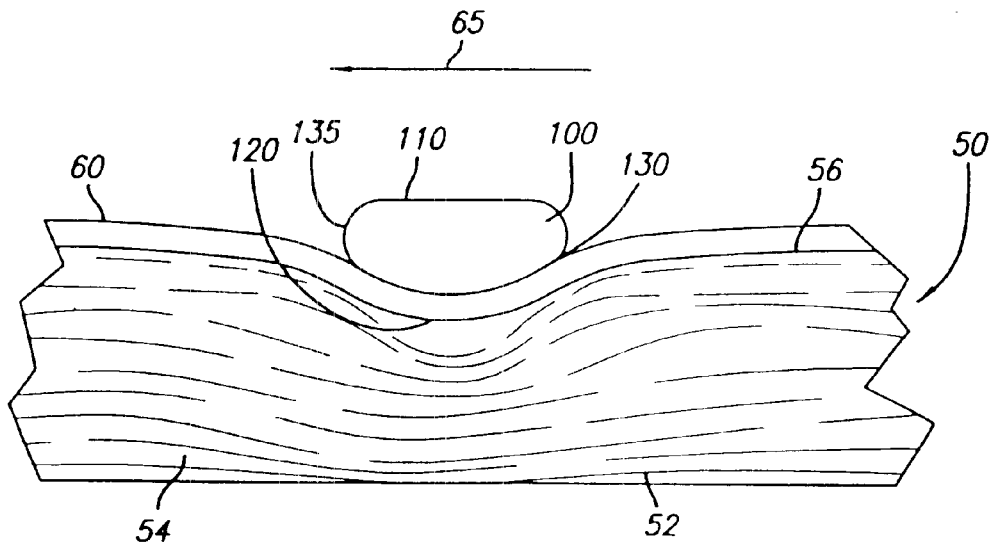
FIG. 8 depicts a cross-sectional view of an embodiment of a stent strut of the present invention having an outer surface configured to minimize trauma to the vessel wall and further having an inner surface configured to reduce the turbulence of the blood flow over the strut.
Figure 9:
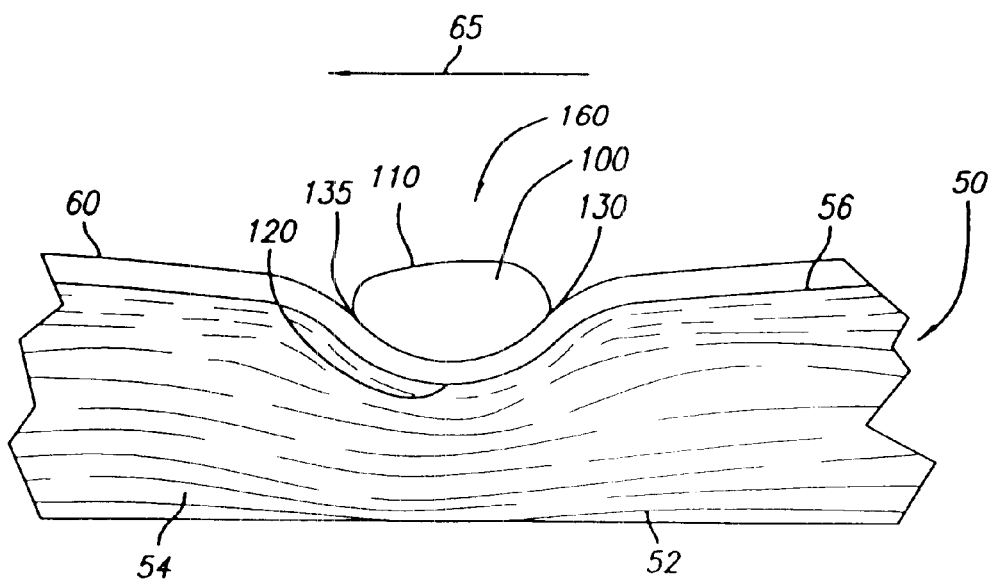
FIG. 9 depicts a cross-sectional view of another embodiment of a stent strut of the present invention having an outer surface configured to minimize trauma to the vessel wall and further having an inner surface configured to be foil shaped.

Referring now to FIGS. 8 and 9, the ideal geometry of the stent inner surface 110 is the shape that least disturbs the blood flow 65, and may not be the same shape that is optimal for the outer surface 120. However, the shape of the ideal inner surface is also a function of the strut width and the amount of strut cross-sectional area needed for strength. As shown in FIG. 8, if the strut material is very strong, then the inner surface would be relatively flat, with rounded edges. To minimize the disturbance of blood flow, the inner surface should provide a smooth transition at the interface between the strut leading edge 130 and the vessel wall 50. Likewise, there should be a smooth transition at the interface between the strut trailing edge 135 and the vessel wall. Such a transition should create the least amount of drag, least amount of pressure drop and reduce the disturbance of the blood flow around the area where the stent strut is imbedded in the vessel wall. Thus, the inner surface should be hydrodynamically designed to disturb the blood flow in a minimal manner.

The overall optimal geometry of the stent strut 100 of the present invention combines an outer surface 120 that minimizes vessel injury with an inner surface 110 whose hydrodynamics minimizes the disturbance to the blood flow 65. Considering the materials of construction currently available for manufacturing stent struts, the strut may require a certain cross-sectional area to meet strength requirements (e.g., greater than that shown in FIG. 8). As shown in FIG. 9, adding material to the stent, while providing hydrodynamics that minimizes the disturbance to the blood flow, yields a wing-like (foil) shape 160. Such an inner surface (foil shaped) has a first slope rising from the leading edge and being towards the incoming blood flow, and has a second slope facing away from the incoming blood flow, such that the first slope is steeper than the second slope. In addition, the second slope may be tapered towards the trailing edge to further decrease the disturbance to the blood flow.

The optimal configuration of the inner surface 110 may not be symmetric relative to a radial vector, and may have a preferred flow direction relative to the blood flow 65. The exact optimal shape, however, would need to be determined via computational fluid dynamic studies, combined with consideration of the strut width and cross-sectional area constraints. Optimizing the geometric shape of the inner surface to one that generates the least amount of hydrodynamic drag on the inner surface will likely give the optimum shape. The inner surface may not be symmetric with respect to the radial axis (FIG. 1B), and should be oriented correctly relative to the blood flow direction. The correct radius of curvature for the inner surface can be determined by studies of optimally deployed stents in cadavaric coronary vessels. In addition, the geometry of the stent struts may change at the junctions of the struts, where stresses on the stent may be concentrated.

Referring now to FIGS. 10–13, the stent struts of the present invention may be fabricated from any of several methods known to those of ordinary skill in the art. For example, laser cutting a pattern in a tube, chemical etching a pattern in tube, electron discharge machining (EDM) a pattern in a tube, or wire extrusion can be utilized. Such methods can be used to form a stent pattern in a flat sheet which is then rolled into a cylinder and made into a tube by welding together the longitudinal edges. Such stent processes require electropolishing, which is well known, to remove processing impurities and form a smooth stent surface.

In manufacturing a stent strut 100 as is illustrated in (FIGS. 4, 8 and 9), a tube of 316L stainless steel or other suitable material is first laser cut to provide a desired pattern of voids defining struts and spines, all in accordance with well known and well established procedures. After the voids have been cut into the tube, the surfaces of the cut tubing may be mechanically polished or electropolished to provide an extremely smooth surface. Electropolishing is a well known technique wherein the workpiece is immersed in an acidic solution and subjected to an electric potential. In the treatment of stainless steel, the procedure not only serves to smooth out the surface, but additionally serves to remove iron from near the surface to leave behind a chromium-rich stratum with enhanced corrosion resistance. The stent is subjected to the electropolishing step for a period of time sufficient to reduce the wall thickness of the stainless steel to an acceptable pre-defined thickness and to obtain a good polish. Alternatively, bead blasting or microsanding may be employed to achieve a sufficiently smooth surface.

Current laser cutting technology fabricates a stent from a metal tube 200 having a wall 210. The focal point of the laser beam 220 is on or in the tube wall. As shown in FIG. 10, movement along two axes—longitudinal (centered) and radial, which may be referred to as "Z" and "alpha" ($\alpha$) respectively—allow the tube to be moved under the laser beam. At all times the beam is orthogonal to the tube surface which results in squared off stent edges. To use laser cutting to give contoured edges requires introducing more degrees of freedom. Thus, another axis perpindicular to the longitudinal axis, referred to as "pitch" (P), is employed (FIG. 11). This pitch axis intersects the beam focal point 220. By rotating the tube about the laser focal point using the pitch axis, strut edges may be accurately cut at an angle as long as the struts lie perpendicular to the tube axis.

By introducing another axis parallel to the longitudinal axis and on the surface of the tube, referred to as "yaw" (Y), the tube 200 can be rotated about the focal point 220 in the other plane (FIG. 12). By rotating the tube in this direction, the strut edges can be cut at an angle as long as the struts lie parallel to the tube axis. If pitch and yaw are combined, providing a four axis laser cutter, the struts edges could be cut at any angle relative to the strut to provide the desired stent strut geometry. By combining multiple axis laser cutting with electropolishing (FIG. 13), one of ordinary skill in the art could fabricate a strut cross section shape as disclosed herein (FIGS. 4, 8 and 9).

Certain current stent struts are extruded or otherwise formed from metal wire, as is known to those of ordinary skill in the art. Wire can be extruded with any cross sectional shape by use of a shaped extrusion die. It is important to note that some strut cross-sectional shapes may not be desirable near or where the struts meet, i.e., at strut junctions. High aspect ratio shapes, where the width is greater than the height or thickness, can cause twisting of the struts as the stent is expanded. Therefore, near and within strut junctions a more rounded profile may be necessary in order for the stent to expand properly.

The stent configuration of the present invention could be used for coronary, carotid, neurological, saphenous vein graft, venous, renal, iliac, biliary, femoral or other peripheral stent designs. The stents may be self-expanding or made to be balloon expandable. There is no inherent limitation on the stent's diameter, length, pattern or overall strut size and as such will be dependent upon a particular application for the stent. Again, the manner and shape of the stents made in accordance with the present invention are numerous and can be made from a tubular segment or alternatively shaped with wire or wire-like meshing. Any of the common material for construction of stents, or new materials of construction, may be employed.

Thus, the stent of the present invention provides an improved strut geometry or shape that may minimize the chance of vessel injury through rupture and dissection of the intima and IEL. In addition, the novel stent struts decrease thrombosis by a reduction in the turbulent flow caused by stent struts. Furthermore, the stent struts of the present invention reduce neointima hyperplasia by reducing the disturbance to the endothelium created by time varying and non-physiologic fluid shear stresses. Thus, the stent geometry disclosed herein has the potential to solve a long sought medical need.

While a particular form of the invention has been illustrated and described, it will also be apparent to those skilled in the art that various modifications can be made without departing from the spirit and scope of the invention. More specifically, it should be clear that the present invention is not limited to tubular type stents nor is it limited to any particular method of forming the underlying stent structure. Accordingly, it is not intended that the invention be limited, except as by the appended claims.

What is claimed is:

1. An endoprosthesis for implanting in a body lumen defined by a wall, comprising;
   at least one strut forming a structural member, the strut having an outer surface, an inner surface and a width, wherein the shape of the outer surface is different from the shape of the inner surface and the outer surface is curved substantially an entire width of the strut, the outer surface being configured to engage and reduced damage to a lumen wall.

2. The endoprosthesis of claim 1, wherein the outer surface is symmetric relative to a radial vector.

3. The endoprosthesis of claim 1, wherein the outer surface is configured with a cross-section formed as a circular arc having a single radius of curvature.

4. The endoprosthesis of claim 3, wherein the radius of curvature of the outer surface is defined by the expression: $r = W \div (2 \sin \theta)$, where r is the radius of curvature of the outer surface, W is a strut width and $\theta$ is an angle in which the lumen wall intercepts the strut.

5. The endoprosthesis of claim 1, wherein the strut further includes a leading edge and a trailing edge, such that there is a first transition zone proximate the leading edge and the outer surface, and there is a second transition zone proximate the trailing edge and the outer surface, wherein the outer surface is configured with a cross-section having a single radius of curvature except at the first and second transition zones.

6. The endoprosthesis of claim 1, wherein the inner surface is non-symmetric relative to a radial vector.

7. The endoprosthesis of claim 2, wherein the inner surface is non-symmetric relative to a radial vector.

8. The endoprosthesis of claim 1, wherein the inner surface is hydrodynamically designed to minimize disturbance of fluid flow over the endoprosthesis.

9. The endoprosthesis of claim 3, wherein the inner surface is hydrodynamically configured to reduce disturbance of fluid flow over the endoprosthesis.

10. The endoprosthesis of claim 1, wherein the inner surface has a preferred fluid flow direction.

11. The endoprosthesis of claim 9, wherein the inner surface has a preferred fluid flow direction.

12. The endoprosthesis of claim 1, wherein the inner surface includes a first slope towards incoming fluid flow and a second slope facing away from incoming fluid flow, and wherein the first slope is steeper than the second slope.

13. The endoprosthesis of claim 12, wherein the inner surface along the second slope is tapered.

14. The endoprosthesis of claim 3, wherein the inner surface is foil shaped.

15. The endoprosthesis of claim 1, the outer surface having more curved surfaces than the inner surface.

16. The endoprosthesis of claim 1, the outer surface having a curve that evenly distributes stresses placed on a body lumen by the endoprosthesis.

17. A stent for implanting in a blood vessel, comprising:

a plurality of struts forming a structural member, each strut having an outer surface, an inner surface and a width, wherein the outer surface is curved substantially an entire width of the strut and is configured to engage and reduce damage to a wall of the blood vessel, and the inner surface is configured to reduce disturbance of blood flow over the stent and has a different shape from the outer surface.

18. The stent of claim 17, wherein the outer surface is configured with a cross-section formed as a circular arc having a single radius of curvature.

19. The stent of claim 18, wherein the inner surface includes a first slope towards incoming blood flow and a second slope facing away from incoming blood flow, such that the first slope is steeper than the second slope.

20. The stent of claim 15, wherein the outer surface is configured with a cross-section having a radius of curvature defined by the expression: $r = W \div (2 \sin \theta)$, where r is the radius of curvature, W is a strut width and $\theta$ is an angle in which the vessel wall intercepts the strut.

21. The stent of claim 20, wherein the inner surface is foil shaped.

22. The stent of claim 17, the outer surface having more curved surfaces than the inner surface.

23. The stent of claim 17, the outer surface having a curve that evenly distributes stresses placed on a body lumen by the stent.

* * * * *

UNITED STATES PATENT AND TRADEMARK OFFICE
CERTIFICATE OF CORRECTION

PATENT NO. : 6,685,737 B1
DATED : February 3, 2004
INVENTOR(S) : Stephen D. Pacetti It is certified that error appears in the above-identified patent and that said Letters Patent is hereby corrected as shown below:

Column 2,
Line 28, change "U.S. Pat. No. 4,512,1338" to -- U.S. Pat. No. 4,512,338 --

Column 5,
Lines 1 and 2, change "strut having an diamond" to -- strut having a diamond --
Lines 3 and 4, change "a stent stent having" to -- a stent having --

Column 6,
Lines 28 and 29, change "blood flowing through the" to -- blood flowing through the --

Column 7,
Line 6, change "defined as the as the midpoints" to -- defined as the midpoints --
Lines 8 and 9, change "defined as the as the midpoints" to -- defined as the midpoints --
Line 64, change "Referring to Fig. 6, The radius" to -- Referring to Fig. 6, the radius --

Column 10,
Lines 53 and 54, change "engage and reduced damage" to -- engage and reduce damage --

Column 12,
Line 18, change "stent of claim 15, wherein" to -- stent of claim 17, wherein --

Signed and Sealed this

Twenty-first Day of September, 2004

JON W. DUDAS
*Director of the United States Patent and Trademark Office*